United States Patent [19]

Hawkins

[11] 4,276,141

[45] Jun. 30, 1981

[54] SOLID STATE ION SELECTIVE ELECTRODES

[75] Inventor: John J. Hawkins, Santa Ana, Calif.

[73] Assignee: Beckman Instruments, Inc., Fullerton, Calif.

[21] Appl. No.: 52,639

[22] Filed: Jun. 27, 1979

Related U.S. Application Data

[63] Continuation-in-part of Ser. No. 880,908, Feb. 24, 1978, abandoned.

[51] Int. Cl.³ ............................................. G01N 27/46
[52] U.S. Cl. .............................. 204/195 M; 204/1 T
[58] Field of Search .............. 204/1 T, 1 A, 195 M, 204/195 F, 195 L

[56] References Cited

U.S. PATENT DOCUMENTS

| 3,448,032 | 6/1969 | Settzo et al. | 204/195 L |
| 3,562,129 | 2/1971 | Simon | 204/195 L |
| 3,598,713 | 8/1971 | Baum et al. | 204/195 L |
| 3,655,526 | 4/1972 | Christian | 204/195 M |
| 3,662,745 | 5/1972 | Cosentino | 204/195 F |
| 3,767,553 | 10/1973 | Brown et al. | 204/195 M |
| 3,856,649 | 12/1974 | Genshaw et al. | 204/195 M |
| 3,857,777 | 12/1974 | Guilbault et al. | 204/195 M |
| 3,926,764 | 12/1975 | Ruzicka et al. | 204/195 M |
| 4,053,381 | 10/1977 | Hamblen et al. | 204/195 M |

FOREIGN PATENT DOCUMENTS

46024 11/0976 United Kingdom .
49537 11/1976 United Kingdom .

OTHER PUBLICATIONS

Cattrall et al., "Analytical Chemistry", vol. 46, No. 14, Dec. 1974, pp. 223-2224.
Baum et al., "Analytica Chimica Acta", vol. 65, (1973), pp. 393-403.
Buck, "Analytical Chemistry", 1974, 46(5):28R-51R.
Cattrall et al., "Analytical Chemistry", 43(13):1905-1906, (1971).
Eyal et al., "Analytical Chemistry", 43(8):1090-1093, (1971).
Fiedler et al., "Analytica Chimica Acta", 67:179-193,(1971).
Frant et al., "Science", 987-988, (Feb., 1970).
Koryta, "Analytica Chimica Acta", 61:329-411, (1972).
Koryta, "Analytica Chimica Acta", 91:1-85, (1977).
Le Blanc, Jr., et al., "Analytical Chemistry", 48(12):1658-1660, (1976).
Band et al., "Intensive Care", 49-52, (1977).
Mascini et al., "Analytica Chimica Acta", 73:375-382, (1974).
Miyada et al., "Clincal Chemistry", 17:27-30,(1971).
Oehme et al., "Analytica Chimica Acta", 86:21-25, (1976).
Petranek et al., "Analytica Chimica Acta", 72:375-380, (1974).
Pioda et al., "Analytical Letters", 2(12):665-674, (1969).
Pretsch et al., "Research Development", 20-24, (Mar. 1974).
Rock et al., "Electrochemical Society Journal", 124:530-531, (1977).
Ryba et al., "Talanta", 23:158-159, (1976).
Pick et al., "Analytica Chimica Acta", 64:477-480, (1973).
Thomas, "Proc. Soc. Analyt. Chem.", 340-342, (Dec. 1974).
Wise et al., "Clinical Chemistry", 16(2):103-106, (1970).

*Primary Examiner*—T. Tung
*Attorney, Agent, or Firm*—R. J. Steinmeyer; Robert R. Meads; Robert S. Frieman

[57] ABSTRACT

A solid state electrode for use in determining ion concentration in an aqueous solution comprising an electrically conductive element; a first lipophilic-hydrophobic (hereinafter referred to as LH) layer in intimate contact with the element; and a second LH layer in intimate contact with the first layer. The first LH layer comprises an adhesive, LH polymer having an intrinsic viscosity of from about 0.4 to about 0.9 ml/g; and an LH plasticizer. The second LH layer comprises a LH polymer having an intrinsic viscosity of from about 1 to about 1.5 ml/g; an LH plasticizer, and an LH ion-selective ligand of the ion to be determined.

Preferably, the first LH layer further comprises an LH charge carrier.

As used herein, the term "lipophilic-hydrophobic (LH)" denotes an organic solvent soluble-water insoluble substance.

60 Claims, 4 Drawing Figures

SOLID STATE ION SELECTIVE ELECTRODES

CROSS-REFERENCES TO RELATED APPLICATIONS

This application is a continuation-in-part of application Ser. No. 880,908, filed Feb. 24, 1978, now abandoned.

BACKGROUND OF THE INVENTION

1. Field of the Invention

This invention relates to an electrode for use in measuring ion concentration. More specifically, this invention relates to a solid electrode for use in measuring unknown ion concentrations in solution.

2. Description of the Prior Art

A review of the ion-selective electrode art is set forth in Buck, *Analytical Chemistry*, 46(5): 28R (1974); Koryta, *Analytica Chimica Acta*, 61:329 (1972); and Koryta, *Analytica Chimica Acta*, 91:1 (1977), said publications and the citations therein being incorporated herein in toto by reference.

In particular, U.S. Pat. No. 3,856,649 discloses a solid state electrode comprising an electrically conductive inner element with a salt disposed on a surface portion thereof. The cation moeity of the salt is a cation form of the conductive inner element. A hydrophilic layer is in intimate contact with the salt. The hydrophilic layer includes a water soluble salt of the anion moeity of the salt. A hydrophobic layer is in intimate contact with the hydrophilic layer.

A very serious problem encountered in using an electrode manufactured according to the teachings of U.S. Pat. No. 3,856,649 is their generally short operable life span.

SUMMARY OF THE INVENTION

This invention is embodied in a solid state electrode for use in determining ion concentration in an aqueous solution and having an operable life span in continuous clinical analyses of greater than one year. This electrode comprises:

(a) an electrically conductive element;

(b) a first lipophilic-hydrophobic (hereinafter referred to as LH) layer in intimate contact with said element, said first layer comprising:
  (i) an adhesive, LH polymer having an intrinsic viscosity of from about 0.4 to about 0.9 ml/g; and
  (ii) an LH plasticizer; and (c) a second LH layer in intimate contact with said first layer, said second layer comprising:
  (i) an LH polymer having an intrinsic viscosity of from about 1 to about 1.5 ml/g;
  (ii) an LH plasticizer; and
  (iii) an LH ion-selective ligand.

Preferably, the first LH layer further comprises an LH charge carrier.

As used herein, the term "lipophilic-hydrophobic (LH)" denotes an organic solvent soluble-water insoluble substance.

DESCRIPTION OF THE PREFERRED EMBODIMENTS

Figure 1:
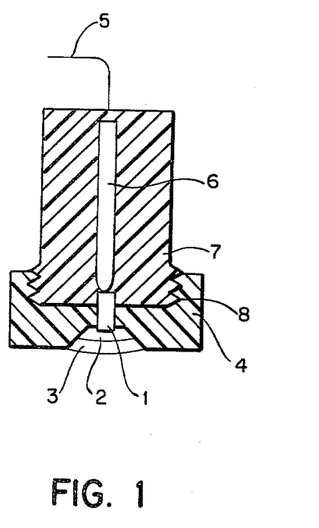
FIG. 1 is a schematic representation of one solid state electrode embodiment within the scope of the instant invention.

A preferred embodiment of the instant invention is shown in FIG. 1. An electrically conductive element 1 is firmly held by an electrically insulating cap 4. The cap 4 has means 8 for holding an electrically insulating stem 7 such that electrical conductor 6 is in electrical communication with element 1. Conductor 6 is in electrical communication with electrically conductive lead 5. A first LH layer 2 is in intimate contact with element 1 and a second LH layer 3 is in intimate contact with the first layer 2.

Figure 2:
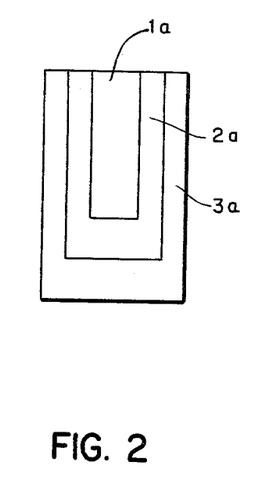
FIG. 2 is a second schematic representation of a solid state electrode within the scope of the instant invention.
Figure 3:
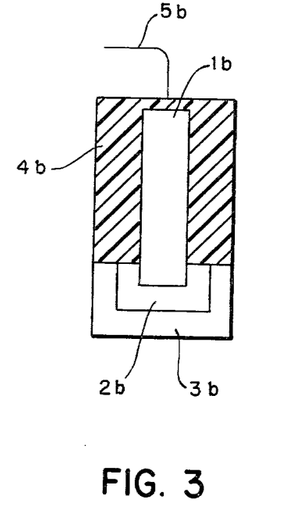
FIG. 3 is a third schematic representation of a solid state electrode within the scope of the instant invention.
Figure 4:
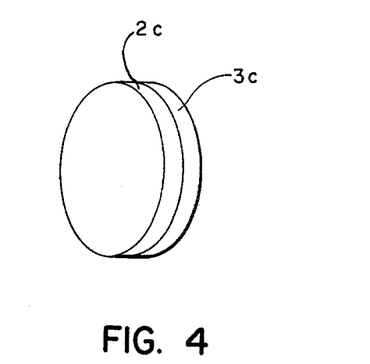
FIG. 4 is a schematic representation of a membrane within the scope of this invention.

The lettered numbers of FIGS. 2-4 depict other embodiments of the corresponding numbered item discussed with respect to FIG. 1 above.

The electrically conductive element 1 of this invention may be any of the numerous items that are commonly used for this purpose. For example, the electrically conductive element 1 can be selected from a group consisting of metals, metal salt coated metals, conductive carbons, conductive metal oxide coated metals, metal-group VI element compositions, compactive metal-metal salt mixtures, compactive metal-conductive metal oxide mixtures, and mixtures thereof. The electrically conductive element 1 is preferably selected from the group consisting of silver, platinum, gold, tin, indium, MX coated silver, copper oxide coated copper, silver oxide coated silver, tin oxide coated tin, reticulated carbon, compactive silver-MX mixtures, wherein M is silver and X is halogen or a group VI element, compactive copper-copper oxide mixture, compactive silver-silver oxide mixture, compactive tin-tin oxide mixture, and mixtures thereof.

X is preferably chlorine or iodine, and more preferably is chlorine.

The shape of the element 1 is not critical and can be dictated by such factors as commercial availability, ease of fabrication, and type and amount of aqueous solution to be assayed.

Contrary to the teachings in U.S. Pat. No. 3,856,649, in the instant invention the layer 2 which is in intimate contact with the element 1 is lipophilic-hydrophobic. This LH layer comprises an adhesive, LH polymer having an intrinsic viscosity of from about 0.4 to about 0.9, preferably from about 0.5 to about 0.7, and more preferably about 0.6 ml/g; and an LH plasticizer.

The adhesive, LH polymer is preferably selected from a group consisting of halogenated and unhalogenated aliphatic and aromatic polymers, copolymers, and terpolymers, block polymers, and grafted polymers thereof, and cycloaliphatic polymers. More preferably, the adhesive, LH polymer is selected from the group consisting of polyurethane, polyvinyl chloride-ethylene copolymer, polyvinyl chloride-propylene copolymer, polyvinyl chloride-butylene copolymer, polyvinyl chloride-ethylhexene copolymer, polyvinyl chloride-isoprene copolymer, polyvinyl chloride-butadiene copolymer, polyvinyl chloride-vinyltoluene copolymer, polyvinyl chloride-styrene copolymer, styrene-ethylene copolymer, styrene-propylene copolymer, styrene-butylene copolymer, styrene-ethylhexene copolymer, styrene-isoprene copolymer, styrene-butadiene copolymer, and styrene-butadiene-acrylonitrile terpolymer.

The LH plasticizer should be compatible in high concentrations with the above described adhesive, LH polymer and should enhance the adhesive characteristics of said polymer. Preferably, the LH plasticizer is selected from a group consisting of phthalates, adipates, trimellitates, nitroaryl alkyl ethers, nitroaryl alkylaryl ethers, nitroaryl arylalkyl ethers, phosphates, phosphonates, and mixtures thereof. More particularly, the LH plasticizer is selected from the group consisting of dialkyl phthalates, dialkylaryl phthalates, diaryl phthalates, diarylalkyl phthalates, dialkyl adipates, dialkylaryl adipates, diaryl adipates, diarylalkyl adipates, trialkyl trimellitates, trialkylaryl trimellitates, triaryl trimellitates, triarylalkyl trimellitates, nitroaryl alkyl ethers, nitroaryl alkylaryl ethers, nitroaryl arylalkyl ethers, dialkyl alkyl phosphonates, dialkyl aryl phosphonates, diaryl aryl phosphonates, diaryl alkyl phosphonates, trialkyl phosphates, trialkylaryl phosphates, triaryl phosphates, triarylalkyl phosphates, and mixtures thereof wherein each alkyl group contains from 8 to 14 carbon atoms and each aryl group contains from 6 to 12 carbon atoms.

More preferably, the LH plasticizer is a lower impedance rendering plasticizer. These lower impedance rendering plasticizers can be, for example, selected from the group consisting of dialkyl adipates, dialkylaryl adipates, diaryl adipates, diarylalkyl adipates, dialkyl alkyl phosphonates, dialkyl aryl phosphonates, diaryl aryl phosphonates, diaryl alkyl phosphonates, trialkyl phosphates, triaryl phosphates, trialkylaryl phosphates, triarylalkyl phosphates, nitroaryl alkyl ethers, nitroaryl alkylaryl ethers, and nitroaryl arylalkyl ethers. It is further preferred that each alkyl group contain from 8 to 12 carbon atoms and be in the normal or iso- alkyl configuration.

Overlaying the LH layer 2 and in intimate contact therewith is a second LH layer 3. This second LH layer comprises an LH polymer having an intrinsic viscosity of from about 1 to about 1.5, preferably from about 1 to about 1.3, and more preferably from about 1.1 to about 1.2 ml/g an LH plasticizer; and an LH ion-selective ligand.

The LH polymer should be of the type that remains strong and durable when highly plasticized. Preferably, this LH polymer is a polyvinyl chloride homopolymer.

The LH plasticizer employed in layer 3 should possess the same desirable properties as described above with respect to the plasticizer employed in layer 2. The preferred plasticizers employed in layer 3 are also the preferred plasticizers employed in layer 2. Furthermore, it is preferred that the same plasticizers be employed in both layers 2 and 3.

The LH ion-selective ligand can be any composition capable of selective metal complexation. Typical LH ion selective ligands include ion selective antibiotics, ion selective macrocyclics, ion selective open chain neutral ligands, ion selective open chain ionic ligands, ion selective inorganic compounds, and mixtures thereof.

The ratio of the above described constituents present in LH layer 2 and LH layer 3 is not critical. However, it is preferred that LH layer 2 comprise from about 15 to about 60, more preferably from about 20 to about 40, and optimally from about 20 to about 30, weight percent of the adhesive, LH polymer; and from about 40 to about 85; more preferably from about 60 to about 80, and optimally from about 70 to about 80 weight percent of the LH plasticizer.

With respect to LH layer 3, this layer preferably comprises from about 20 to about 80, more preferably from about 25 to about 45, and optimally about 28 to about 32, weight percent of said LH polymer; from about 40 to about 79.991, more preferably from about 50 to about 74.92, and optimally from about 66.5 to about 71.9, weight percent of said LH plasticizer; and from about 0.009 to about 10, more preferably from about 0.08 to about 5, and optimally from about 0.1 to about 1.5, weight percent of the LH ion-selective ligand.

The dielectric constants of LH layer 2 and LH layer 3 are not critical. However, for the determination of the concentration of a monovalent cation in an aqueous solution, it is preferred that LH layer 3 have a dielectric constant of from about 3 to about 4.5 at 60 cycles.

For the determination of the concentration of a divalent cation in an aqueous solution, it is preferred that LH layer 3 have a dielectric constant of from about 5 to about 14 at 60 cycles.

The exact constituents chosen from the above description for use in element 1, LH layer 2, and LH layer 3 for the determination of a particular ion is not critical. (One will, of course, select a lipophilic ion-selective ligand suitable for the ion to be determined.) However, by selectively choosing said constituents, one can optimize the solid state electrode's sensitivity to the concentration of the particular ion to be determined. For example, for the determination of potassium ion concentration it is preferred that element 1 be selected from a group consisting of MX coated silver and compacted mixture of silver and MX, wherein M and X are as defined above.

The adhesive, LH polymer to be employed in layer 2 for use in the determination of potassiuum ion concentration is preferably slected from a group consisting of polyvinyl chloride-propylene copolymer and styrene-isoprene copolymer.

The LH plasticizer to be employed in both layer 2 and layer 3 for use in the determination of potassium ion concentration is preferably selected from a group consisting of dialkyl adipate and diaryl adipate. More preferably, the plasticizer to be employed in said layers is dioctyl adipate.

The LH ion-selective ligand to be employed in layer 3 for use in the determination of potassium ion concentration is preferably selected from a group consisting of potassium selective antibiotics, potassium selective macrocyclics, potassium selective open chain neutral ligands, potassium selective open chain ionic ligands, potassium selective-inorganic compounds, and mixtures thereof. More preferably, the LH ion-selective ligand is selected from the group consisting of nonactin, homologues of nonactin, gramicidin, valinomycin, dimethyldibenzo-30-crown-10, dibenzo-18-crown-6 and potassium zinc ferrocyanide. Valinomycin is the LH ion-selective ligand most preferably used in the determination of potassium ion concentration.

The composition of the first LH layer 2 can be prepared, in general, by mixing the adhesive, LH polymer and the LH plasticizer together. To the mixture is added a solvent, such as a 50:50 by volume xylene:1,2-dichloroethane. This mixture should be thoroughly mixed. If desired, one can heat the mixture to about 50° C. to reduce the time required for complete mixing. The mixture is then cooled to room temperature.

The composition of the second LH layer 3 can be prepared, in general, by mixing the LH polymer and the LH plasticizer together. To the mixture is added a solvent, such as cyclohexanone. This mixture should be thoroughly mixed. If desired, one can heat the mixture to about 50° C. to reduce the time required for complete mixing. When the mixture has cooled to room temperature, an LH ion-selective ligand can be added to the mixture and the mixture again mixed. The ion-selective ligand can be added as a solution wherein the solvent is, for example, cyclohexanone.

In a preferred embodiment, the first LH layer 2 of this invention's solid state electrode further comprises an LH charge carrier. Contrary to the teachings of U.S. Pat. No. 3,856,649, the particular charge carrier employed in this embodiment of the instant invention is not critical and is lipophilic-hydrophobic. For example, the LH charge carrier can be selected from a group consisting of ion selective antibiotics, ion selective macrocyclics, ion selective open chain neutral ligands, ion selective open chain ionic ligands, ion selective inorganic compounds, organometallic charge carriers, and mixtures thereof.

The LH charge carrier and the LH ion-selective ligand to be employed in layer 2 and layer 3, respectively, of this preferred embodiment for use in the determination of potassium ion concentration are preferably independently selected from a group consisting of potassium selective antibiotics, potassium selective macrocyclics, potassium selective open chain neutral ligands, potassium selective open chain ionic ligands, potassium selective inorganic compounds, and mixtures thereof.

More preferably, the charge carrier is selected from the group consisting of nonactin, homologues of nonactin, gramicidin; valinomycin, dimethyldibeno-30-crown-10, dibenzo-18-crown-6, and potassium zinc ferrocyanide. Valinomycin is the charge carrier most preferably used in the determination of potassium ion concentration.

The LH plasticizer employed in this preferred embodiment need not be a lower impedance rendering plasticizer and are selected from the group consisting of trialkyl trimellitate, trialkylaryl trimellitate, triaryl trimellitate, triarylalkyl trimellitate, dialkyl alkyl phosphonates, dialkyl aryl phosphonate, diaryl aryl phosphonate, diaryl alkyl phosphonate, nitroaryl alkyl ethers, nitroaryl alkylaryl ethers, and nitroaryl arylalkyl ethers. It is further preferred that each alkyl group contain from 8 to 12 carbon atoms and be in the normal or isoalkyl configuration.

The LH plasticizer to be employed in both layer 2 and layer 3 for use in the determination of potassium ion concentration in this preferred embodiment is preferably selected from a group consisting of trialkyl trimellitates, trialkylaryl trimellitates, triaryl trimellitates, and triarylalkyl trimellitates. More preferably, the plasticizer to be employed in said layers is selected from the group consisting of trioctyl trimellitate, triisononyl trimellitate, tri-n-nonyl trimellitate, triphenyl trimellitate, trioctylphenyl trimellitate, and tridecylphenyl trimellitate.

The ratio of the constituents present in a charge carrier containing LH layer 2 is not critical. However, it is preferred that a charge carrier containing LH layer 2 comprise from about 15 to about 85, more preferably from about 20 to about 35, and optimally from about 20 to about 30, weight percent of the adhesive, LH polymer; from about 10 to about 84.99, more preferably from about 62.5 to about 79.95, and optimally from about 69 to about 79.92 weight percent of the LH plasticizer; and from about 0.01 to about 5, more preferably from about 0.05 to about 2.5, and optimally from about 0.08 to about 1, weight percent of said LH charge carrier.

The composition of a charge carrier containing first layer 2 can be prepared, in general, by mixing the adhesive, LH polymer and the LH plasticizer together. To the mixture is added a solvent, such as a 50:50 by volume xylene:1,2-dichloroethane. This mixture should be thoroughly mixed. If desired, one can heat the mixture to about 50° C. to reduce the time required for complete mixing. When the mixture has cooled to room temperature, an LH charge carrier can be added to the mixture and the mixture again mixed. The charge carrier can be added as a solution wherein the solvent is, for example, cyclohexanone.

The solid state electrode can be fabricated in a number of different ways depending on the desired configuration as well as one's manufacturing capabilities. If an electrode such as shown in FIG. 1 is desired, the first LH layer 2 is formed by placing a predetermined amount of the mixture of the composition of layer 2 over element 1 and drying the coated element at room temperature. If desired, this sequence can be repeated more than one time.

Over dried layer 2 is then placed a predetermined amount of the mixtuure of the composition of layer 3 and also dried at room temperature. If desired, this latter sequence can also be repeated more than one time, and is preferably repeated at least once.

The solid state electrodes of FIGS. 2-3 can be prepared by simply sequentially dipping the element in the appropriate solution the desired number of times and allowing the wet coating to dry between successive dips.

The solid state electrodes within the scope of this invention can be employed to determine ion concentration in an aqueous solution. The solution can, for example, be water, biological fluids, such as blood and urine, and numerous other liquids and environments wherein one desires to perform such a measurement.

The following examples are provided for the purpose of further illustration only and are not intended to be limitations on the disclosed invention.

EXAMPLE 1

Compounding of Composition for Layer 2

Flowell 470 brand polyvinyl chloride-propylene (2.6 grams) and 7.4 grams dioctyl adipate were dissolved in 30 ml cyclohexanone in a bottle. A cap was placed on the bottle and the capped bottle was rapidly agitated to thoroughly mix the contents. The capped bottle was placed on a roller and the mixing was maintained until the components formed a clear liquid. A heat lamp was used to raise the temperature to approximately 50° C. to reduce the time required for complete mixing.

The bottle and its contents were then cooled to room temperature.

EXAMPLE 2

Compounding of Composition for Layer 3

Into a bottle was placed 3 grams of a polyvinyl chloride homopolymer having an inherent viscosity of 1.13 ml/g. Next, 7 grams of dioctyl adipate was placed into the bottle. These components were then mixed to a uniform consistency. Cyclohexanone (50 ml) was added to the above mixture. A cap was placed on the bottle and the capped bottle was rapidly agitated to thoroughly mix its contents. The capped bottle was placed on a roller and the mixing was maintained until the components formed a clear liquid. A heat lamp was used to raise the temperature to approximately 50° C. to reduce the time required for complete mixing.

An aliquot (10% by weight) of the above prepared composition was placed in a second bottle. Valinomycin (7.5 mg) in about 20 μl cyclohexanone was then added to the mixture in the second bottle. The bottle was capped and placed on a roller for about 20 minutes to thoroughly mix the valinomycin.

EXAMPLE 3

Fabrication of Membrane

A cap of the type schematically shown in FIG. 1 as numeral 4 having firmly held therein an element comprising a compacted mixture of silver-silver chloride was selected. 35 μl of the mixture prepared in Example 1 was then deposited over the element and allowed to dry at room temperature for about 24 hours. Next 35 μl of the mixture prepared in Example 2 was then deposited over the first layer and also allowed to dry at room temperature for 24 hours. A second 35 μl aliquot of the mixture prepared in Example 2 was deposited over the dry first aliquot and allowed to dry in air for an additional 24 hours.

EXAMPLE 4

Life Span

The solid state electrode prepared in Example 3 was evaluated for Nernstian activity and the data obtained therefrom is shown in Table I.

EXAMPLE 5

Compounding of Composition for a Charge Carrier Containing Layer 2

Into a bottle was placed 9.5 grams of a 10% solution of Flowell 470 brand polyvinyl chloride-propylene in 50:50 by volume xylene:1,2-dichloroethane. Next, 1.4988 grams of trioctyl trimellitate were placed into the bottle. A cap was placed on the bottle and the capped bottle was rapidly agitated to thoroughly mix the contents. The capped bottle was placed on a roller and the mixing was maintained until the components formed a clear liquid. A heat lamp was used to raise the temperature to approximately 50° C. to reduce the time required for complete mixing.

The bottle and its contents were then cooled to room temperature and 2.4 mg of valinomycin in cyclohexanone were added to the mixture. The bottle was recapped and placed on a roller for about 20 minutes to thoroughly mix the valinomycin.

EXAMPLE 6

Compounding of Composition for Layer 3

Into a bottle was placed 3.05 grams of a polyvinylchloride homopolymer having an inherent viscosity of 1.13. Next, 6.90 grams of trioctyl trimellitate were placed into the bottle. These components were then mixed to a uniform consistency. Cyclohexanone (50 ml) was added to the above mixture. A cap was placed on the bottle and the capped bottle was rapidly agitated to thoroughly mix its contents. The capped bottle was placed on a roller and the mixing was maintained until the components formed a clear liquid. A heat lamp was used to raise the temperature to approximately 50° C. to reduce the time required for complete mixing.

The bottle and its contents were then cooled to room temperature and 0.05 grams of valinomycin in cyclohexanone were added to the mixture. The bottle was recapped and placed on a roller for about 20 minutes to thoroughly mix the valinomycin.

EXAMPLE 7

Fabrication of Membrane

A cap of the type schematically shown in FIG. 1 as numeral 4 having firmly held therein an element comprising a compacted mixture of silver-silver chloride was selected. 35 μl of the mixture prepared in Example 5 was then deposited over the element and allowed to dry at room temperature for about 24 hours. Next 35 μl of the mixture prepared in Example 6 was then deposited over the first layer and also allowed to dry at room temperature for 24 hours. A second μl aliquot of the mixture prepared in Example 6 was deposited over the dry first aliquot and allowed to dry in air for an additional 24 hours.

EXAMPLE 7

Life Span

The solid state electrode prepared in Example 7 was evaluated for Nernstian activity and the data obtained therefrom is shown in Table I. The electrode was then installed in a clinical analyzer on about Feb. 1, 1977 and used continually therein in clinical assays for potassium until about Jan. 23, 1978. The electrode was then removed from the analyzer and checked for Nernstian activity and the data obtained therefrom is also shown in Table I.

TABLE I

| | Nernstian Activity of Solid State Electrodes Within Scope of Invention | | | |
|---|---|---|---|---|
| | Span/Decade of Molar Concentration, mV | | | |
| Date | $10^{-1}$ to $10^{-2}$ | $10^{-2}$ to $10^{-3}$ | $10^{-3}$ to $10^{-4}$ | $10^{-4}$ to $10^{-5}$ |
| | Example 4 Data | | | |
| 11/27/78 | 49 | 51 | 63 | 58.5 |
| 1/19/79 | 50 | 55 | 57 | 56.5 |
| | Example 7 Data | | | |
| 2/1/77 | 55 | 58.5 | 58.5 | N.D.* |
| 1/23/78 | 51 | 56.5 | 52.5 | N.D. |

*N.D. denotes "not determined".

As is well known to those skilled in the art, an acceptable minimum Nernstian span value is 50 mV for monovalent cations, such as potassium. Therefore Table I shows that the solid state electrodes within the scope of the invention, as exemplified by the electrodes of Examples 4 and 7, are capable of accurately assaying ion concentrations over a prolonged period of time.

EXAMPLE 8

Prior Art Electrode Within Scope of U.S. Pat. No. 3,856,649

Acrylamide (5% cross-linkable) was mixed with 0.1 M KCl (aqueous) to form a mixture containing 20 weight percent acrylamide and 80 weight percent 0.1 M KCl (aqueous). Methylethyl ketone (MEK) peroxide was added to the mixture to act as a polymerization initiator.

About 25 μl of this unpolymerized mixture was placed over a compacted silver-silver chloride element, which element was firmly held in a cap of the type described in Example 3, supra. The silver-silver chloride covered element was placed in an oven and the mixture polymerized in situ at 60° C. to form a hydrophilic layer.

The outside hydrophobic layer was prepared as set forth in Example 2, supra. About 35 μl of the mixture of Example 2 was placed over the hydrophilic layer and allowed to dry at room temperature for about 16 hours. This latter step was repeated once.

Data obtained with this electrode is shown in Table II.

EXAMPLE 9

Prior Art Electrode Within Scope of U.S. Pat. No. 3,856,649

Glycerin and an acrylate monomer were mixed to form a 50:50 by weight mixture. To this mixture was added a 0.1 M KCl (aqueous) solution to form a mixture comprising 20 weight percent 0.1 M KCl (aqueous) and 80 weight percent of said glycerin acrylate mixture. MEK peroxide was added to the mixture to act as a polymerization initiator.

About 25 μl of this unpolymerized mixture was placed over a compacted silver-silver chloride element, which element was firmly held in a cap of the type described in Example 3, supra. The silver-silver chloride covered element was placed in an oven and the mixture polymerized in situ at 60° C. to form a hydrophilic layer.

The outside hydrophobic layer was prepared as set forth in Example 2, supra. About 35 μl of the mixture of Example 2 was placed over the hydrophilic layer and allowed to dry at room temperature for about 16 hours. This latter step was repeated once.

Data obtained with this electrode is also shown in Table II.

TABLE II

Nernstian Activity of Solid State Prior Art Elctrodes

| Date | Span/Decade of Molar Concentration, mV | | | |
|---|---|---|---|---|
| | $10^{-1}$–$10^{-2}$ | $10^{-2}$–$10^{-3}$ | $10^{-3}$–$10^{-4}$ | $10^{-4}$–$10^{-5}$ |
| Example 8 Data | | | | |
| 11/26/76 | 55 | 57 | 58 | 56 |
| 11/27/76[1] | 30 | 81 | 17 | N.D.* |
| Example 9 Data | | | | |
| 11/29/76 | 45 | 55.5 | 57.5 | 52.5 |
| 12/1/76 | 52 | 39 | 53 | 43 |
| 12/3/76 | 30 | 42 | 48 | 42 |

*N.D. means "not determined"
[1]Microscopic examination revealed hydrophobic layer ruptured due to excessive swelling of the inside hydrophilic layer caused by excessive water vapor absorption.

The above data of Table II clearly indicates the short life span of the prior art solid state electrode as taught in U.S. Pat. No. 3,856,649. These electrodes yielded unacceptable results after a period of just a few days.

The membrane within the scope of the instant invention is also useful in solid state ion-selective electrodes of the ISE-FET type.

Based on this disclosure, many other modifications and ramifications will naturally suggest themselves to those skilled in the art of ion sensitive electrodes. These are intended to be comprehended as within the scope of this invention.

The embodiments of the invention in which an exclusive property or privilege is claimed are defined as follows:

1. A solid state electrode for use in determination of ion concentration in an aqueous solution comprising:
   (a) an electrically conductive element;
   (b) a first lipophilic-hydrophobic layer in intimate contact with said element, said first layer comprising:
      (i) an adhesive, lipophilic-hydrophobic polymer having an intrinsic viscosity of from about 0.4 to about 0.9 ml/g; and
      (ii) a lipophilic-hydrophobic plasticizer; and
   (c) a second lipophilic-hydrophobic layer in intimate contact with said first layer, said second layer comprising:
      (i) a lipophilic-hydrophobic polymer having an intrinsic viscosity of from about 1 to about 1.5 ml/g;
      (ii) a lipophilic-hydrophobic plasticizer; and
      (iii) a lipophilic-hydrophobic ion-selective ligand.

2. The electrode of claim 1 wherein:
   (a) said electrically conductive element is selected from a group consisting of metals, metal salt coated metals, conductive carbons, conductive metal oxide coated metals, metal-group VI element compositions, compacted metal-metal salt mixtures, compacted metal-conductive metal oxide mixtures, and mixtures thereof;
   (b) said first layer comprises:
      (i) said adhesive, lipophilic-hydrophobic polymer selected from a group consisting of halogenated and unhalogenated aliphatic and aromatic polymers, copolymers, and terpolymers, block polymers, and grafted polymers thereof, and cycloaliphatic polymers; and
      (ii) said lipophilic-hydrophobic plasticizer selected from a group consisting of phthalates, adipates, trimellitates, nitroaryl alkyl ethers, nitroaryl alkylaryl ethers, nitroaryl arylalkyl ethers, phosphates, phosphonates, and mixtures thereof; and
   (c) said second layer comprises:
      (i) a polyvinyl chloride homopolymer as said lipophilic-hydrophobic polymer;
      (ii) said lipophilic-hydrophobic plasticizer selected from a group consisting of phthalates, adipates, trimellitates, nitroaryl alkyl ethers, nitroaryl alkylaryl ethers, nitroaryl arylalkyl ethers, phosphates, phosphonates, and mixtures thereof;
      (iii) said lipophilic-hydrophobic ion selective ligand selected from a group consisting of ion selective antibiotics, ion selective macrocyclics, ion selective open chain neutral ligands, ion selective open chain ionic ligands, ion selective inorganic compounds, and mixtures thereof.

3. The electrode of claim 2 wherein:
   (a) said electrically conductive element is selected from the group consisting of silver, platinum, gold, tin, indium, MX coated silver, copper oxide coated copper, silver oxide coated silver, tin oxide coated tin, reticulated carbon, compacted silver-MX mixtures, wherein M is silver and X is selected from a group consisting of halogen and group VI elements, compacted copper-copper oxide mixture, compacted silver-silver oxide mixture, compacted tin-tin oxide mixture, and mixtures thereof;
   (b) said first layer comprises:

(i) said adhesive, lipophilic-hydrophobic polymer selected from a group consisting of polyvinyl chloride-ethylene copolymer, polyvinyl chloride-polypropylene copolymer, polyvinyl chloride-butylene copolymer, polyvinyl chloride-ethylhexene copolymer, polyvinyl chloride-isoprene copolymer, polyvinyl chloride-butadiene copolymer, polyvinyl chloride-vinyltoluene copolymer, polyvinyl chloride-styrene copolymer, styrene-ethylene copolymer, styrene-propylene copolymer, styrene-butylene copolymer, styrene-butadiene copolymer, styrene-ethylhexene copolymer, styrene-isoprene copolymer, and styrene-butadiene-acrylonitrile terpolymer; and (ii) said liphophilic-hydrophobic plasticizer selected from the group consisting of dialkyl phthalates, dialkylaryl phthalates, diaryl phthalates, diarylalkyl phthalates, dialkyl adipates, dialkylaryl adipates, diaryl adipates, diarylalkyl adipates, trialkyl trimellitates, trialkylaryl trimellitates, triaryl trimellitates, triarylalkyl trimellitates, nitroaryl alkyl ethers, nitroaryl alkylaryl ethers, nitroaryl arylalkyl ethers, dialkyl alkyl phosphonates, dialkyl aryl phosphonates, diaryl aryl phosphonates, diaryl alkyl phosphonates, trialkyl phosphates, trialkylaryl phosphates, triaryl phosphates, triarylalkyl phosphates, and mixtures thereof, wherein each alkyl group contains from 8 to 14 carbon atoms and each aryl group contains from 6 to 12 carbon atoms; and (c) said second layer comprises:

(i) said polyvinyl chloride homopolymer;

(ii) said lipophilic-hydrophobic plasticizer selected from the group consisting of dialkyl phthalates, dialkylaryl phthalates, diaryl phthalates, diarylalkyl phthalates, dialkyl adipates, dialkylaryl adipates, diaryl adipates, diarylalkyl adipates, trialkyl trimellitates, trialkylaryl trimellitates, triaryl trimellitates, triarylalkyl trimellitates, nitroaryl alkyl ethers, nitroaryl alkylaryl ethers, nitroaryl arylalkyl ethers, dialkyl alkyl phosphonates, dialkyl aryl phosphonates, diaryl aryl phosphonates, diaryl alkyl phosphonates, trialkyl phosphates, trialkylaryl phosphates, triaryl phosphates, triarylalkyl phosphates, and mixtures thereof, wherein each alkyl group contains from 8 to 14 carbon atoms and each aryl group contains from 6 to 12 carbon atoms; and (iii) said liphophilic-hydrophobic ion-selective ligand.

4. The electrode of claim 3 wherein:

X is selected from a group consisting of chlorine and iodine; and said lipophilic-hydrophobic plasticizer employed in both said first layer and said second layer is independently selected from the group consisting of dialkyl adipates, dialkylaryl adipates, diaryl adipates, diarylalkyl adipates, dialkyl alkyl phosphonates, dialkyl aryl phosphonates, diaryl aryl phosphonates, diaryl alkyl phosphonates, trialkyl phosphonates, triaryl phosphates, trialkylaryl phosphates, triarylalkyl phosphates, nitroaryl alkyl ethers, nitroaryl alkylaryl ethers, and nitroaryl arylalkyl ethers, wherein said alkyl groups contain from 8 to 12 carbon atoms and are in a normal or iso -alkyl configuration.

5. The electrode of claims 1, 2, 3 or 4 wherein said first layer comprises from about 15 to about 60 weight percent of said adhesive lipophilic-hydrophobic polymer and from about 40 to about 85 weight percent of said lipophilic-hydrophobic plasticizer; and said second layer comprises from about 20 to about 80 weight percent of said lipophilic-hydrophobic polymer, from about 40 to about 79.991 weight percent of said lipophilic-hydrophobic plasticizer; and from about 0.009 to about 10 weight percent of said lipophilic-hydrophobic ion-selective ligand.

6. The electrode of claims 1, 2, 3 or 4 wherein said first layer comprises from about 20 to about 40 weight percent of said adhesive, lipophilic-hydrophobic polymer and from about 60 to about 80 weight percent of said lipophilic-hydrophobic plasticizer; and said second layer comprises from about 25 to about 45 weight percent of said lipophilic-hydrophobic polymer, from about 50 to about 74.92 weight percent of said lipophilic-hydrophobic plasticizer, and from about 0.08 to about 5 weight percent of said lipophilic-hydrophobic ion-selective ligand.

7. The electrode of claims 1, 2, 3, or 4 wherein said first layer comprises from about 20 to about 30 weight percent of said adhesive, lipophilic-hydrophobic polymer and from about 70 to about 80 weight percent of said lipophilic-hydrophobic plasticizer; and said second layer comprises from about 28 to about 32 weight percent of said lipophilic-hydrophobic polymer, from about 66.5 to about 71.9 weight percent of said lipophilic-hydrophobic plasticizer, and from about 0.1 to about 1.5 weight percent of said lipophilic-hydrophobic ion-selective ligand.

8. The electrode of claims 1, 2, 3 or 4 wherein said adhesive, lipophilic-hydrophobic polymer in said first layer has an intrinsic viscosity of from about 0.5 to about 0.7 ml/g and wherein said lipophilic-hydrophobic polymer in said second layer has an intrinsic viscosity of from about 1.0 to about 1.3 ml/g.

9. The electrode of claims 1, 2, 3 or 4 wherein said adhesive, lipophilic-hydrophobic polymer in said first layer has an intrinsic viscosity of about 0.6 ml/g and wherein said lipophilic-hydrophobic polymer in said second layer has an intrinsic viscosity of about 1.1 to about 1.2 ml/g.

10. The electrode of claims 1, 2, 3 or 4 for use in the determination of monovalent cation concentration in an aqueous solution wherein said second layer has a dielectric constant of from about 3 to about 4.5 at 60 cycles.

11. The solid-state electrode of claims 1, 2, 3 or 4 for use in the determination of divalent cation concentration in an aqueous solution wherein said second layer has a dielectric constant of from about 5 to about 14 at 60 cycles.

12. The electrode of claim 1 for use in the determination of potassium ion concentration in an aqueous solution comprising:

(a) said electrically conductive element selected from a group consisting of MX coated silver and compacted mixtures of silver and MX, wherein M is silver and X is selected from a group consisting of halogen and group VI elements;

(b) said first layer comprising:

(i) said adhesive, lipophilic-hydrophobic polymer selected from a group consisting of polyvinyl chloride-propylene copolymer and styrene-isoprene copolymer; and (ii) said lipophilic-hydrophobic plasticizer selected from a group consisting of dialkyl adipates and diaryl adipates, wherein each alkyl group contains from about 8 to about 14 carbon atoms and each aryl group contains from 6 to 12 carbon atoms; and (c) said second layer comprising:
 (i) a polyvinyl chloride homopolymer as said lipophilic-hydrophobic polymer;
 (ii) said lipophilic-hydrophobic plasticizer selected from a group consisting of dialkyl adipates and diaryl adipates, wherein each alkyl group contains from 8 to about 14 carbon atoms and each aryl group contains from 6 to 12 carbon atoms; and
 (iii) said lipophilic-hydrophobic ion-selective ligand selected from a group consisting of potassium selective antibiotics, potassium selective macrocyclics, potassium selective open chain neutral ligands, potassium selective open chain ionic ligands, and potassium selective inorganic compounds, and mixtures thereof.

13. The electrode of claim 12 wherein X is selected from the group consisting of chlorine and iodine, wherein said adhesive lipophilic-hydrophobic polymer in said first layer has an intrinsic viscosity of from about 0.5 to about 0.7 ml/g, wherein each of said alkyl groups contains from 8 to 12 carbon atoms; and wherein said polyvinyl chloride homopolymer has an intrinsic viscosity of from about 1.0 to about 1.3 ml/g.

14. The electrode of claim 13 wherein X is chlorine, wherein said adhesive, lipophilic-hydrophobic polymer in said first layer has an intrinsic viscosity of about 0.6 ml/g; wherein said lipophilic-hydrophobic plasticizer in said first and second layer is dioctyl adipate; wherein said polyvinyl chloride homopolymer has an intrinsic viscosity of from about 1.1 to about 1.2 ml/g; and wherein said lipophilic-hydrophobic ion-selective ligand is valinomycin.

15. The electrode of claims 1, 2, 3, 4, 12 or 13 wherein said lipophilic-hydrophobic plasticizer in said first and second layers is the same.

16. A membrane for use in determination of ion concentration in an aqueous solution comprising:
 (a) a first lipophilic-hydrophobic layer comprising:
  (i) an adhesive, lipophilic-hydrophobic polymer having an intrinsic viscosity of from about 0.4 to about 0.9 ml/g; and
  (ii) an lipophilic-hydrophobic plasticizer; and
 (c) a second lipophilic-hydrophobic layer in intimate contact with said first layer, said second layer comprising:
  (i) a lipophilic-hydrophobic polymer having an intrinsic viscosity of from about 1 to about 1.5 ml/g;
  (ii) a lipophilic-hydrophobic plasticizer; and
  (iii) a lipophilic-hydrophobic ion-selective ligand.

17. The membrane of claim 16 wherein:
(a) said first layer comprises:
 (i) said adhesive, lipophilic-hydrophobic polymer selected from a group consisting of halogenated and unhalogentated aliphatic and aromatic polymers, copolymers, and terpolymers, block polymers, and grafted polymers thereof, and cycloaliphatic polymers; and
 (ii) said lipophilic-hydrophobic plasticizer selected from a group consisting of phthalates, adipates, trimellitates, nitroaryl alkyl ethers, nitroaryl alkylaryl ethers, nitroaryl arylalkyl ethers, phosphates, phosphonates, and mixtures thereof; and
(b) said second layer comprises:
 (i) a polyvinyl chloride homopolymer as said lipophilic-hydrophobic polymer;
 (ii) said lipophilic-hydrophobic plasticizer selected from a group consisting of phthalates, adipates, trimellitates, nitroaryl alkyl ethers, nitroaryl alkylaryl ethers, nitroaryl arylalkyl ethers, phosphates, phosphonates, and mixtures thereof;
 (iii) said lipophilic-hydrophobic ion selective ligand selected from a group consisting of ion selective antibiotics, ion selective macrocyclics, ion selective open chain neutral ligands, ion selective open chain ionic ligands, ion selective inorganic compounds, and mixtures thereof.

18. The membrane of claim 17 wherein:
(a) said first layer comprises:
 (i) said adhesive, lipophilic-hydrophobic polymer selected from a group consisting of polyvinyl chloride-ethylene copolymer, polyvinyl chloride-polypropylene copolymer, polyvinyl chloride-butylene copolymer, polyvinyl chloride-ethylhexene copolymer, polyvinyl chloride-isoprene copolymer, polyvinyl chloride-butadiene copolymer, polyvinyl chloride-vinyltoluene copolymer, polyvinyl chloride-styrene copolymer, styrene-ethylene copolymer, styrene-propylene copolymer, styrene-butylene copolymer, styrene-butadiene copolymer, styrene-ethylhexene copolymer, styrene-isoprene copolymer, and styrene-butadiene-acrylonitrile terpolymer; and
 (ii) said liphophilic-hydrophobic plasticizer selected from the group consisting of dialkyl phthalates, dialkylaryl phthalates, diaryl phthalates, diarylalkyl phthalates, dialkyl adipates, dialkylaryl adipates, diaryl adipates, diarylalkyl adipates, trialkyl trimellitates, trialkylaryl trimellitates, triaryl trimellitates, triarylalkyl trimellitates, nitroaryl alkyl ethers, nitroaryl alkylaryl ethers, nitroaryl arylalkyl ethers, dialkyl alkyl phosphonates, dialkyl aryl phosphonates, diaryl aryl phosphonates, diaryl alkyl phosphonates, trialkyl phosphates, trialkylaryl phosphates, triaryl phosphates, triarylalkyl phosphates, and mixtures thereof, wherein each alkyl group contains from 8 to 14 carbon atoms and each aryl group contains from 6 to 12 carbon atoms; and
(b) said second layer comprises:
 (i) said polyvinyl chloride homopolymer;
 (ii) said lipophilic-hydrophobic plasticizer selected from the group consisting of dialkyl phthalates, dialkylalkyl phthalates, diaryl phthalates, diarylalkyl phthalates, dialkyl adipates, dialkylaryl adipates, diaryl adipates, diarylalkyl adipates, trialkyl trimellitates, trialkylaryl trimellitates, triaryl trimellitates, triarylalkyl trimellitates, nitroaryl alkyl ethers, nitroaryl alkylaryl ethers, nitroaryl arylalkyl ethers, dialkyl alkyl phosphonates, dialkyl aryl phosphonates, diaryl aryl phosphonates, diaryl alkyl phosphonates, trialkyl phosphates, trialkylaryl phosphates, triaryl phosphates, triarylalkyl phosphates, and mixtures thereof, wherein each alkyl group contains from 8 to 14 carbon atoms and each aryl group contains from 6 to 12 carbon atoms; and
 (iii) said lipophilic-hydrophobic ion-selective ligand.

19. The membrane of claim 18 wherein:
said lipophilic-hydrophobic plasticizer employed in both said first layer and said second layer is independently selected from the group consisting of dialkyl adipates, dialkylaryl adipates, diaryl adipates, diarylalkyl adipates, dialkyl alkyl phosphonates, dialkyl aryl phosphonates, diaryl aryl phosphonates, diaryl alkyl phosphonates, trialkyl phosphates, triaryl phosphates, trialkylaryl phosphates, triarylalkyl phosphates, nitroaryl alkyl ethers, nitroaryl alkylaryl ethers, and nitroaryl arylalkyl ethers, wherein said alkyl groups contain from 8 to 12 carbon atoms and are in a normal or iso- alkyl configuration.

20. The membrane of claims 16, 17, 18, or 19 wherein said first layer comprises from about 15 to about 60 weight percent of said adhesive lipophilic-hydrophobic polymer and from about 40 to about 85 weight percent of said lipophilic-hydrophobic plasticizer; and said second layer comprises from about 20 to about 80 weight percent of said lipophilic-hydrophobic polymer, from about 40 to about 79.991 weight percent of said lipophilic-hydrophobic plasticizer; and from about 0.009 to about 10 weight percent of said lipophilic-hydrophobic ion-selective ligand.

21. The membrane of claims 16, 17, 18, or 19 wherein said first layer comprises from about 20 to about 40 weight percent of said adhesive, lipophilic-hydrophobic polymer and from about 60 to about 80 weight percent of said lipophilic-hydrophobic plasticizer; and said second layer comprises from about 25 to about 45 weight percent of said lipophilic-hydrophobic polymer, from about 50 to about 74.92 weight percent of said lipophilic-hydrophobic plasticizer, and from about 0.08 to about 5 weight percent of said lipophilic-hydrophobic ion-selective ligand.

22. The membrane of claims 16, 17, 18 or 19 wherein said first layer comprises from about 20 to about 30 weight percent of said adhesive, lipophilic-hydrophobic polymer and from about 70 to about 80 weight percent of said lipophilic-hydrophobic plasticizer; and said second layer comprises from about 28 to about 32 weight percent of said lipophilic-hydrophobic polymer, from about 66.5 to about 71.9 weight percent of said lipophilic-hydrophobic plasticizer, and from about 0.1 to about 1.5 weight percent of said lipophilic-hydrophobic ion-selective ligand.

23. The membrane of claims 16–18 or 19 wherein said adhesive, lipophilic-hydrophobic polymer in said first layer has an intrinsic viscosity of from about 0.5 to about 0.7 ml/g and wherein said lipophilic-hydrophobic polymer in said second layer has an intrinsic viscosity of from about 1.0 to about 1.3 ml/g.

24. The membrane of claims 16–18 or 19 wherein said adhesive, lipophilic-hydrophobic polymer in said first layer has an intrinsic viscosity of about 0.6 ml/g and wherein said lipophilic-hydrophobic polymer in said second layer has an intrinsic viscosity of about 1.1 to about 1.2 ml/g.

25. The membrane of claims 16–18 or 19 for use in the determination of monovalent cation concentration in an aqueous solution wherein said second layer has a dielectric constant of from about 3 to about 4.5 at 60 cycles.

26. The membrane of claims 16–18 or 19 for use in the determination of divalent cation concentration in an aqueous solution wherein said second layer has a dielectric constant of from about 5 to about 14 at 60 cycles.

27. The membrane of claim 16 for use in the determination of potassium ion concentration in an aqueous solution comprising:
(a) said first layer comprising:

(i) said adhesive, lipophilic-hydrophobic polymer selected from a group consisting of polyvinyl chloride-propylene copolymer and styrene-isoprene copolymer; and
   (ii) said lipophilic-hydrophobic plasticizer selected from a group consisting of dialkyl adipates and diaryl adipates, wherein each alkyl group contains from about 8 to about 14 carbon atoms; and each aryl group contains from 6 to 12 carbon atoms; and
(b) said second layer comprising:
   (i) a polyvinyl chloride homopolymer as said lipophilic-hydrophobic polymer
   (ii) said lipophilic-hydrophobic plasticizer selected from a group consisting of dialkyl adipates and diaryl adipates, wherein each alkyl group contains from 8 to about 14 carbon atoms and each aryl group contains from 6 to 12 carbon atoms; and
   (iii) said lipophilic-hyodrophobic ion-selective ligand selected from a group consisting of potassium selective antiobiotics, potassium selective macrocylics, potassium selective open chain neutral ligands, potassium selective open chain ionic ligands, and potassium selective inorganic compounds, and mixtures thereof.

28. The membrane of claim 27 wherein said adhesive lipophilic-hydrophobic polymer in said first layer has an intrinsic viscosity of from about 0.5 to about 0.7 ml/g, wherein each of said alkyl groups contains from 8 to 12 carbon atoms; and wherein said polyvinyl chloride homopolymer has an intrinsic viscosity of from about 1.0 to about 1.3 ml/g.

29. The membrane of claim 28 wherein said adhesive, lipophilic-hydrophobic polymer in said first layer has an intrinsic viscosity of about 0.6 ml/g; wherein said lipophilic-hydrophobic plasticizer in said first and second layer is dioctyl adipate; wherein said polyvinyl chloride homopolymer has an intrinsic viscosity of from about 1.1 to about 1.2 ml/g; and wherein said lipophilic-hydrophobic ion-selective ligand is valinomycin.

30. The membrane of claims 16, 17, 18, 19, 27, or 28 wherein said lipophilic-hydrophobic plasticizer in said first and second layers is the same.

31. The electrode of claim 1 wherein said first layer further comprises a lipophilic-hydrophobic charge carrier.

32. The electrode of claim 31 wherein:
(a) said electrically conductive element is selected from a group consisting of metals, metal salt coated metals, conductive carbons, conductive metal oxide coated metals, metal-group VI element compositions, compacted metal-metal salt mixtures, compacted metal-conductive metal oxide mixtures, and mixtures thereof;
(b) said first layer comprises:
   (i) said adhesive, lipophilic-hydrophobic polymer selected from a group consisting of halogenated and unhalogenated aliphatic and aromatic polymers, copolymers, and terpolymers, block polymers, and grafted polymers thereof, and cycloaliphatic polymers;
   (ii) said lipophilic-hydrophobic plasticizer selected from a group consisting of phthalates, adipates, trimellitates, nitroaryl alkyl ethers, nitroaryl alkylaryl ethers, nitroaryl arylalkyl ethers, phosphates, phosphonates, and mixtures thereof;

(iii) said lipophilic-hydrophobic charge carrier selected from a group consisting of ion selective antibiotics, ion selective macrocyclics, ion selective open chain neutral ligands, ion selective open chain ionic ligands, ion selective inorganic compounds, organometallic charge carriers, and mixtures thereof; and (c) said second layer comprises:
  (i) a polyvinyl chloride homopolymer as said lipophilic-hydrophobic polymer;
  (ii) said lipophilic-hydrophobic plasticizer selected from a group consisting of phthalates, adipates, trimellitates, nitroaryl alkyl ethers, nitroaryl alkylaryl ethers, nitroaryl arylalkyl ethers, phosphates, phosphonates, and mixtures thereof;
  (iii) said lipophilic-hydrophobic ion selective ligand selected from a group consisting of ion selective antibiotics, ion selective macrocyclics, ion selective open chain neutral ligands, ion selective open chain ionic ligands, ion selective inorganic compounds, and mixtures thereof.

33. The electrode of claim 32 wherein:
(a) said electrically conductive element is selected from the group consisting of silver, platinum, gold, tin, indium, MX coated silver, copper oxide coated copper, silver oxide coated silver, tin oxide coated tin, reticulated carbon, compacted silver-MX mixtures, wherein M is silver and X is selected from a group consisting of halogen and group VI elements, compacted copper-copper oxide mixture, compacted silver-silver oxide mixture, compacted tin-tin oxide mixture, and mixtures thereof;
(b) said first layer comprises:
  (i) said adhesive, lipophilic-hydrophobic polymer selected from a group consisting of polyvinyl chloride-ethylene copolymer, polyvinyl chloride-polypropylene copolymer, polyvinyl chloride-butylene copolymer, polyvinyl chloride-ethylhexene copolymer, polyvinyl chloride-isoprene copolymer, polyvinyl chloride-butadiene copolymer, polyvinyl chloride-vinyltoluene copolymer, polyvinyl chloride-styrene copolymer, styrene-ethylene copolymer, styrene-propylene copolymer, styrene-butylene copolymer, styrene-butadiene copolymer, styrene-ethylhexene copolymer, and styrene-butadiene-acrylonitrile terpolymer;
  (ii) said lipophilic-hydrophobic plasticizer selected from the group consisting of dialkyl phthalates, dialkylaryl phthalates, diaryl phthalates, diarylalkyl phthalates, dialkyl adipates, dialkylaryl adipates, diaryl adipates, diarylalkyl adipates, trialkyl trimellitates, trialkylaryl trimellitates, triaryl trimellitates, triarylalkyl trimellitates, nitroaryl alkyl ethers, nitroaryl alkylaryl ethers, nitroaryl arylalkyl ethers, dialkyl alkyl phosphonates, dialkyl aryl phosphonates, diaryl aryl phosphonates, diaryl alkyl phosphonates, trialkyl phosphates, trialkylaryl phosphates, triaryl phosphates, triarylalkyl phosphates, and mixtures thereof, wherein each alkyl group contains from 8 to 14 carbon atoms and each aryl group contains from 6 to 12 carbon atoms; and
  (iii) said lipophilic-hydrophobic charge carrier; and
(c) said second layer comprises:
  (i) said polyvinyl chloride homopolymer;
  (ii) said lipophilic-hydrophobic plasticizer selected from the group consisting of dialkyl phthalates, dialkylaryl phthalates, diaryl phthalates, diarylalkyl phthalates, dialkyl adipates, dialkylaryl adipates, diaryl adipates, diarylalkyl adipates, trialkyl trimellitates, trialkylaryl trimellitates, triaryl trimellitates, triarylalkyl trimellitates, nitroaryl alkyl ethers, nitroaryl alkylaryl ethers, nitroaryl arylalkyl ethers, dialkyl alkyl phosphonates, dialkyl aryl phosphonates, diaryl aryl phosphonates, diaryl alkyl phosphonates, trialkyl phosphates, trialkylaryl phosphates, triaryl phosphates, triarylalkyl phosphates, and mixtures thereof, wherein each alkyl group contains from 8 to 14 carbon atoms and each aryl group contains from 6 to 12 carbon atoms; and
  (iii) said lipophilic-hydrophobic ion-selective ligand.

34. The electrode of claim 33 wherein X is selected from a group consisting of chlorine and iodine; and
  said lipophilic-hydrophobic plasticizer employed in both said first and said second layer is independently selected from the group consisting of trialkyl trimellitates, trialkylaryl trimellitates, triaryl trimellitates, triarylalkyl trimellitates, dialkyl alkyl phosphonates, dialkyl aryl phosphonates, diaryl aryl phosphonates, diaryl alkyl phosphonates, nitroaryl alkyl ethers, nitroaryl alkylaryl ethers, and nitroaryl arylalkyl ethers, wherein said alkyl groups contain 8 to 12 carbon atoms and are in a normal or iso- alkyl configuration.

35. The electrode of claims 31, 32, 33 or 34 wherein said first layer comprises from about 15 to about 85 weight percent of said adhesive lipophilic-hydrophobic polymer, from about 10 to about 84.99 weight percent of said lipophilic-hydrophobic plasticizer, and from about 0.01 to about 5 weight percent of said lipophilic-hydrophobic charge carrier; and said second layer comprises from about 20 to about 80 weight percent of said liphophilic-hydrophobic polymer, from about 40 to about 79.991 weight percent of said lipophilic-hydrophobic plasticizer; and from about 0.009 to about 10 weight percent of said lipophilic-hydrophobic ion-selective ligand.

36. The electrode of claims 31, 32, 33, or 34 wherein said first layer comprises from about 20 to about 35 weight percent of said adhesive, lipophilic-hydrophobic polymer, from about 62.5 to about 79.5 weight percent of said lipophilic-hydrophobic plasticizer, and from about 0.05 to about 2.5 weight percent of said lipophilic-hydrophobic charge carrier; and said second layer comprises from about 25 to about 45 weight percent of said lipophilic-hydrophobic polymer, from about 50 to about 74.92 weight percent of said lipophilic-hydrophobic plasticizer, and from about 0.08 to about 5 weight percent of said lipophilic-hydrophobic ion-selective ligand.

37. The electrode of claims 31, 32, 33 or 34 wherein said first layer comprises from about 20 to about 30 weight percent of said adhesive, lipophilic-hydrophobic polymer, from about 69 to about 79.92 weight percent of said lipophilic-hydrophobic plasticizer, and from about 0.08 to about 1 weight percent of said lipophilic-hydrophobic charge carrier; and said second layer comprises from about 28 to about 32 weight percent of said lipophilic-hydrophobic polymer, from about 66.5 to about 71.9 weight percent of said lipophilic-hydrophobic plasticizer, and from about 0.1 to about 1.5 weight percent of said lipophilic-hydrophobic ion-selective ligand.

38. The electrode of claims 31–33 or 34 wherein said adhesive, lipophilic-hydrophobic polymer in said first layer has an intrinsic viscosity of from about 0.5 to about 0.7 ml/g and wherein said lipophilic-hydrophobic polymer in said second layer has an intrinsic viscosity of from about 1.0 to about 1.3 ml/g.

39. The electrode of claims 31–33 or 34 wherein said adhesive, lipophilic-hydrophobic polymer in said first layer has an intrinsic viscosity of about 0.6 ml/g and wherein said lipophilic-hydrophobic polymer in said second layer has an intrinsic viscosity of about 1.1 to about 1.2 ml/g.

40. The electrode of claims 31–33 or 34 for use in the determination of monovalent cation concentration in an aqueous solution wherein said second layer has a dielectric constant of from about 3 to about 4.5 at 60 cycles.

41. The solid-state electrode of claims 31, 32, 33 or 34 for use in the determination of divalent cation concentration in an aqueous solution wherein said second layer has a dielectric constant of from about 5 to about 14 at 60 cycles.

42. The electrode of claim 31 for use in the determination of potassium ion concentration in an aqueous solution comprising:
(a) said electrically conductive element selected from a group consisting of MX coated silver and compacted mixtures of silver and MX, wherein M is silver and X is selected from a group consisting of halogen and group VI elements;
(b) said first layer comprising:
(i) said adhesive, lipophilic-hydrophobic polymer selected from a group consisting of polyvinyl chloride-propylene copolymer and styrene-isoprene copolymer;
(ii) said lipophilic-hydrophobic plasticizer selected from a group consisting of trialkyl trimellitates, trialkylaryl trimellitates, triaryl trimellitates, and triarylalkyl trimellitates, wherein each alkyl group contains from about 8 to about 14 carbon atoms and each aryl group contains from 6 to 12 carbon atoms; and
(iii) said lipophilic-hydrophobic charge carrier; and
(c) said second layer comprising:
(i) polyvinyl chloride homopolymer as said lipophilic-hydrophobic polymer;
(ii) said lipophilic-hydrophobic plasticizer selected from a group consisting of trialkyl trimellitates, trialkylaryl trimellitates, triaryl trimellitates, and triarylalkyl trimellitates, wherein each alkyl group contains from 8 to about 14 carbon atoms and each aryl group contains from 6 to 12 carbon atoms; and
(iii) said lipophilic-hydrophobic ion-selective ligand selected from a group consisting of potassium selective antibiotics, potassium selective macrocylics, potassium selective open chain neutral ligands, potassium selective open chain ionic ligands, potassium selective inorganic compounds, and mixtures thereof.

43. The electrode of claim 42 wherein X is selected from the group consisting of chlorine and iodine, wherein said adhesive lipophilic-hydrophobic polymer in said first layer has an intrinsic viscosity of from about 0.5 to about 0.7 ml/g, wherein each of said alkyl groups contains from 8 to 12 carbon atoms; and wherein said polyvinyl chloride homopolymer has an intrinsic viscosity of from about 1.0 to about 1.3 ml/g.

44. The electrode of claim 43 wherein X is chlorine, wherein said adhesive, lipophilic-hydrophobic polymer in said first layer has an intrinsic viscosity of about 0.6 ml/g; wherein said lipophilic-hydrophobic plasticizer in said first and second layer is selected from the group consisting of trioctyl trimellitate, triisononyl trimellitate, tri-n-nonyl trimellitate, triphenyl trimellitate, trioctylphenyl trimellitate, and tridecylphenyl trimellitate; wherein said polyvinyl chloride homopolymer has an intrinsic viscosity of from about 1.1 to about 1.2 ml/g; and wherein said ion-selective ligand is valinomycin.

45. The electrode of claim 44 wherein said lipophilic-hydrophobic charge carrier is valinomycin.

46. A membrane for use in determination of ion concentrations in an aqueous solution comprising:
(a) a first lipophilic-hydrophobic layer comprising:
(i) an adhesive, lipophilic-hydrophobic polymer having an intrinsic viscosity of from about 0.4 to about 0.9 ml/g;
(ii) a lipophilic-hydrophobic plasticizer; and
(iii) a lipophilic-hydrophobic charge carrier; and
(b) a second lipophilic-hydrophobic layer in intimate contact with said first layer, said second layer comprising:
(i) a lipophilic-hydrophobic polymer having an intrinsic viscosity of from about 1 to about 1.5 ml/g;
(ii) a lipophilic-hydrophobic plasticizer; and
(iii) a lipophilic-hydrophobic ion-selective ligand.

47. The membrane of claim 46 wherein:
(a) said first layer comprises:
(i) said adhesive, lipophilic-hydrophobic polymer selected from a group consisting of halogenated and unhalogenated aliphatic and aromatic polymers, copolymers, and terpolymers, block polymers, and grafted polymers thereof, and cycloaliphatic polymers;
(ii) said lipophilic-hydrophobic plasticizer selected from a group consisting of phthalates, adipates, trimellitates, nitroaryl alkyl ethers, nitroaryl alkylaryl ethers, nitroaryl arylalkyl ethers, phosphates, phosphonates, and mixtures thereof;
(iii) said lipophilic-hydrophobic charge carrier selected from a group consisting of ion selective antibiotics, ion selective macrocyclics, ion selective open chain neutral ligands, ion selective open chain ionic ligands, ion selective inorganic compounds, organometallic charge carriers, and mixtures thereof; and
(b) said second layer comprises:
(i) a polyvinyl chloride homopolymer as said lipophilic-hydrophobic polymer;
(ii) said lipophilic-hydrophobic plasticizer selected from a group consisting of phthalates, adipates, trimellitates, nitroaryl alkyl ethers, nitroaryl alkylaryl ethers, nitroaryl arylalkyl ethers, phosphates, phosphonates, and mixtures thereof;
(iii) said lipophilic-hydrophobic ion selective ligand selected from a group consisting of ion selective antibiotics, ion selective macrocyclics, ion selective open chain neutral ligands, ion selective open chain ionic ligands, ion selective inorganic compounds, and mixtures thereof.

48. The membrane of claim 47 wherein:
(a) said first layer comprises:
(i) said adhesive, lipophilic-hydrophobic polymer selected from a group consisting of polyvinyl chloride-ethylene copolymer, polyvinyl chloride-polypropylene copolymer, polyvinyl chloride-butylene copolymer, polyvinyl chloride-ethylhexane copolymer, polyvinyl chloride-isoprene copolymer, polyvinyl chloride-butadiene copolymer, polyvinyl chloride-vinyltoluene copolymer, polyvinyl chloride-styrene copolymer, styrene-ethylene copolymer, styrene-propylene copolymer, styrene-butylene copolymer, styrene-butadiene copolymer, styrene-ethylhexane copolymer, and styrene-butadiene-acrylonitrile terpolymer;

(ii) said lipophilic-hydrophobic plasticizer selected from the group consisting of dialkyl phthalates, dialkylaryl phthalates, diaryl phthalates, diarylalkyl phthalates, dialkyl adipates, dialkylaryl adipates, diaryl adipates, diarylalkyl adipates, trialkyl trimellitates, trialkylaryl trimellitates, triaryl trimellitates, triarylalkyl trimellitates, nitroaryl alkyl ethers, nitroaryl alkylaryl ethers, nitroaryl arylalkyl ethers, dialkyl alkyl phosphonates, dialkyl aryl phosphonates, diaryl aryl phosphonates, diaryl alkyl phosphonates, trialkyl phosphates, trialkylaryl phosphates, triaryl phosphates, triarylalkyl phosphates, and mixtures thereof, wherein each alkyl group contains from 8 to 14 carbon atoms and each aryl group contains from 6 to 12 carbon atoms; and (iii) said lipophilic-hydrophobic charge carrier; and (b) said second layer comprises:

(i) said polyvinyl chloride homopolymer;

(ii) said lipophilic-hydrophobic plasticizer selected from the group consisting of dialkyl phthalates, dialkylaryl phthalates, diaryl phthalates, diarlalkyl phthalates, dialkyl adipates, dialkylaryl adipates, diaryl adipates, diarylalkyl adipates, trialkyl trimellitates, trialkylaryl trimellitates, triaryl trimellitates, triarylalkyl trimellitates, nitroaryl alkyl ethers, nitroaryl alkylaryl ethers, nitroaryl arylalkyl ethers, dialkyl alkyl phosphonates, dialkyl aryl phosphonates, diaryl aryl phosphonates, diaryl alkyl phosphonates, trialkyl phosphates, trialkylaryl phosphates, triaryl phosphates, triarylalkyl phosphates, and mixtures thereof, wherein each alkyl group contains from 8 to 14 carbon atoms and each aryl group contains from 6 to 12 carbon atoms; and (iii) said lipophilic-hydrophobic ion-selective ligand.

49. The membrane of claim 48 wherein:
said lipophilic-hydrophobic plasticizer employed in both said first and said second layer is independently selected from the group consisting of trialkyl trimellitates, trialkylaryl trimellitates, triaryl trimellitates, triarylalkyl trimellitates, dialkyl alkyl phosphonates, dialkyl aryl phosphonates, diaryl aryl phosphonates, diaryl alkyl phosphonates, nitroaryl alkyl ethers, nitroaryl alkylaryl ethers, and nitroaryl arylalkyl ethers, wherein said alkyl groups contain 8 to 12 carbon atoms and are in a normal or iso-alkyl configuration.

50. The membrane of claims 46, 47, 48 or 49 wherein said first layer comprises from about 15 to about 85 weight percent of said adhesive lipophilic-hydrophobic polymer, from about 10 to about 84.99 weight percent of said lipophilic-hydrophobic plasticizer, and from about 0.01 to about 5 weight percent of said lipophilic-hydrophobic charge carrier; and said second layer comprises from about 20 to about 80 weight percent of said lipophilic-hydrophobic polymer, from about 40 to about 79.991 weight percent of said lipophilic-hydrophobic plasticizer; and from about 0.009 to about 10 weight percent of said lipophilic-hydrophobic ion-selective ligand.

51. The membrane of claims 46, 47, 48 or 49 wherein said first layer comprises from about 20 to about 35 weight percent of said adhesive, lipophilic-hydrophobic polymer, from about 62.5 to about 79.5 weight percent of said lipophilic-hydrophobic plasticizer, and from about 0.05 to about 2.5 weight percent of said lipophilic-hydrophobic charge carrier; and said second layer comprises from about 25 to about 45 weight percent of said lipophilic-hydrophobic polymer, from about 50 to about 74.92 weight percent of said lipophilic-hydrophobic plasticizer, and from about 0.08 to about 5 weight percent of said lipophilic-hydrophobic ion-selective ligand.

52. The membrane of claims 46, 47, 48 or 49 wherein said first layer comprises from about 20 to about 30 weight percent of said adhesive, lipophilic-hydrophobic polymer, from about 69 to about 79.92 weight percent of said lipophilic-hydrophobic plasticizer, and from about 0.08 to about 1 weight percent of said lipophilic-hydrophobic charge carrier; and said second layer comprises from about 28 to about 32 weight percent of said lipophilic-hydrophobic polymer, from about 66.5 to about 71.9 weight percent of said lipophilic-hydrophobic plasticizer, and from about 0.1 to about 1.5 weight percent of said lipophilic-hydrophobic ion-selective ligand.

53. The membrane of claims 46, 47, 48 or 49 wherein said adhesive, lipophilic-hydrophobic polymer in said first layer has an intrinsic viscosity of from about 0.5 to about 0.7 ml/g and wherein said lipophilic-hydrophobic polymer in said second layer has an intrinsic viscosity of from about 1.0 to about 1.3 ml/g.

54. The membrane of claims 46, 47, 48 or 49 wherein said adhesive, lipophilic-hydrophobic polymer in said first layer has an intrinsic viscosity of about 0.6 ml/g and wherein said lipophilic-hydrophobic polymer in said second layer has an intrinsic viscosity of about 1.1 to about 1.2 ml/g.

55. The membrane of claims 46, 47, 48 or 49 for use in the determination of monovalent cation concentration in an aqueous solution wherein said second layer has a dielectric constant of from about 3 to about 4.5 at 60 cycles.

56. The membrane of claims 46, 47, 48 or 49 for use in the determination of divalent cation concentration in an aqueous solution wherein said second layer has a dielectric constant of from about 5 to about 14 at 60 cycles.

57. The membrane of claim 46 for use in the determination of potassium ion concentration in an aqueous solution comprising:

(a) said first layer comprising:
  (i) said adhesive, lipophilic-hydrophobic polymer selected from a group consisting of polyvinyl chloride-propylene copolymer and styrene-isoprene copolymer;
  (ii) said lipophilic-hydrophobic plasticizer selected from a group consisting of trialkyl trimellitates, trialkylaryl trimellitates, triaryl trimellitates, and triarylalkyl trimellitates, wherein each alkyl group contains from about 8 to about 14 carbon atoms and each aryl group contains from 6 to 12 carbon atoms; and
  (iii) said lipophilic-hydrophobic charge carrier; and
(b) said second layer comprising:

(i) a polyvinyl chloride homopolymer as said lipophilic-hydrophobic polymer;
(ii) said lipophilic-hydrophobic plasticizer selected from a group consisting of trialkyl, trimellitates, trialkylaryl trimellitates, triaryl trimellitates, and triarylalkyl trimellitates, wherein each alkyl group contains from 8 to about 14 carbon atoms and each aryl group contains from 6 to 12 carbon atoms; and
(iii) said lipophilic-hydrophobic ion-selective ligand selected from a group consisting of potassium selective antibiotics, potassium selective macrocylics; potassium selective opn chain neutral ligands, potassium selective open chain ionic ligands, potassium selective inorganic compounds, and mixtures thereof.

58. The membrane of claim 57 wherein said adhesive lipophilic-hydrophobic polymer in said first layer has an intrinsic viscosity of from about 0.5 to about 0.7 ml/g, wherein each of said alkyl groups contains from 8 to 12 carbon atoms; and wherein said polyvinyl chloride homopolymer has an intrinsic viscosity of from about 1.0 to about 1.3 ml/g.

59. The membrane of claim 58 wherein said adhesive, lipophilic-hydrophobic polymer in said first layer has an intrinsic viscosity of about 0.6 ml/g; wherein said lipophilic-hydrophobic plasticizer in said first and second layer is selected from a group consisting of trioctyl trimellitate, triisononyl trimellitate, tri-n-nonyl trimellitate, triphenyl trimellitate, trioctylphenyl trimellitate, and tridecylphenyl trimellitate; wherein said polyvinyl chloride homopolymer has an intrinsic viscosity of from about 1.1 to about 1.2 ml/g; and wherein said ion-selective ligand is valinomycin.

60. The membrane of claim 59 wherein said lipophilic-hydrophobic charge carrier is valinomycin.

* * * * *